US005768725A

United States Patent [19]

Brenn

[11] Patent Number: 5,768,725

[45] Date of Patent: Jun. 23, 1998

[54] SURGERY PATIENT HEADREST

[75] Inventor: Bruce Randall Brenn, Landenberg, Pa.

[73] Assignee: The Nemours Foundation, Jacksonville, Fla.

[21] Appl. No.: 731,417

[22] Filed: Oct. 15, 1996

Related U.S. Application Data

[62] Division of Ser. No. 621,894, Mar. 26, 1996, Pat. No. 5,596,780, which is a continuation of Ser. No. 346,406, Nov. 29, 1994, abandoned.

[51] Int. Cl.[6] ............................ A47C 20/00; A61B 19/00

[52] U.S. Cl. .................................. 5/636; 128/869; 5/637; 5/643

[56] References Cited

U.S. PATENT DOCUMENTS

| | | | |
|---|---|---|---|
| D. 282,803 | 3/1986 | Righini | 5/636 |
| D. 316,451 | 4/1991 | Carnathan et al. | D24/64 |
| 2,587,196 | 2/1952 | Morecroft | 5/640 |
| 3,327,330 | 6/1967 | McCullough | 5/636 |
| 3,369,548 | 2/1968 | Moore et al. | 128/303 |
| 3,763,509 | 10/1973 | Mittendorf | 5/640 |
| 4,259,757 | 4/1981 | Watson | 5/434 |
| 4,346,488 | 8/1982 | Eary, Sr. | 5/643 |
| 4,783,865 | 11/1988 | Stotler | 5/655 |
| 5,007,122 | 4/1991 | Daughdrill | 5/434 |
| 5,129,705 | 7/1992 | Wray | 5/636 |
| 5,305,754 | 4/1994 | Honeywell et al. | 128/869 |

FOREIGN PATENT DOCUMENTS

| | | | |
|---|---|---|---|
| 0248635 | 3/1926 | United Kingdom | 5/636 |

OTHER PUBLICATIONS

Children's Medical Ventures, Inc. Instructions for Use of Bendy Bumper™, Jun. 1993.

Action Products, Inc., Action® Operating Room Pads and Positioners Brochure Jan. 3, 1990.

*Primary Examiner*—Steven N. Meyers

*Assistant Examiner*—Robert G. Santos

*Attorney, Agent, or Firm*—J. Michael Martinez de Andino; McGuire, Woods, Battle & Boothe, L.L.P.; Jeffrey C. Lew

[57] ABSTRACT

A headrest which can be used on an operating table to maintain the head of a supine, unconscious patient in steady position for the surgeon to conduct an operation is described. The headrest has a low profile to provide maximum unobstructed access to the top, forehead, sides and face of the head. The headrest includes two, tapered, elongated lobes rigidly spaced apart in a V-shape configuration which allows one headrest to fit many different size heads. In use, the patient's head is wedged at points of tangency between the lobes. The V-shape configuration also permits the surgeon to easily adjust the head position to a new, steady position with only minor head movement, and therefore, reduced risk of dislodging the patient's breathing tube.

2 Claims, 3 Drawing Sheets

SURGERY PATIENT HEADREST

This is a division of application Ser. No. 08/621,894 now U.S. Pat. No. 5,596,780 filed Mar. 26, 1996, which is a continuation of application Ser. No. 08/346,406 filed Nov. 29, 1994, now abandoned.

FIELD OF THE INVENTION

This invention relates to a device for positioning the head of a surgery patient.

BACKGROUND AND SUMMARY OF THE INVENTION

Prior to surgery, the anesthetist normally inserts a breathing tube in the trachea through the mouth of the anesthetized patient. In many cases, in order to most safely and expeditiously intubate the unconscious patient, the head should be in an intubating position, sometimes referred to as the "sniffing position". That is, the head is slightly elevated and the neck is extended. For surgery which can be done on the body in the supine position, the patient's head can remain in the intubating position after intubation if the surgery is to be performed on a part of the body distant from the head, such as a leg or the chest. However, if the surgery is to be done on or near the head, the patient's head will be placed in an operating position most convenient for conducting the surgery and which can be different from the intubating position.

Traditionally, various types of support devices, such as soft, gel-filled rings or padded structures, hereinafter collectively referred to as "head rings", and pillows are used to position the head of surgery patients. Intubation is usually completed quickly relative to the overall length of the operation. Therefore, traditional devices, especially pillows, are designed primarily to position the head for surgery and not necessarily with intubating in mind. Conventional head rings are typically so large that they interfere with intubation. If the head is moved off the ring, the anesthetist may need to dedicate one hand to support the patient's head while intubating. This is awkward for the anesthetist. Furthermore, once the patient is intubated, movement of the patient's head to place it on a head ring increases the risk of inadvertent extubation.

Generally, traditional head rings are adapted to fit heads of selected size ranges. That is, one size fits few. Hence it is necessary for a well-supplied operating room to store several different size head rings. Pediatric facilities may require many sizes and/or different types of head rings because head sizes vary considerably with age between infancy and adolescence. In addition to adding clutter in the operating room, the proliferation of head rings presents the problem of selecting the correct size for each patient. Frequently, this is done by trial and error which prolongs the overall procedure. Even the smallest commercially available head rings are too big to fit some neo-natal infants and very small children.

Accordingly, it is an object of the present invention to provide a surgery patient headrest which overcomes the disadvantages of articles known for this purpose. More particularly, it is an object to provide a headrest which is adapted to position the head for both intubating and surgery. The headrest can be used to support the head firmly in the intubating position so that the anesthetist can use two hands to intubate. It can also be used directly thereafter, without lifting the head from the headrest, to position the head for the operation, thereby reducing the risk of unintentional extubation. An advantage of the present invention is that the headrest permits the anesthetist or surgeon, hereinafter collectively referred to as "the surgeon," to rapidly and easily change the patient's head position to gain optimum access to the site of the surgical procedure.

Another object of the invention is to provide a single size headrest which fits many head sizes and shapes, and more specifically, to provide a single size headrest which can accommodate the extremely wide range of head sizes encountered in pediatric surgery.

Yet another object of this invention is to provide a headrest which contacts the patient's head at very few points such that the head is, to a great extent, free from confinement. It is a feature of the present invention that the surgeon has greatly unrestricted access to the top and posterior portions of the patient's head. This feature is especially useful in surgery which involves the head and face. Conventional pillows and head rings do not afford as much access.

Accordingly, there is provided a surgical patient headrest comprising a first elongated lobe having a first longitudinal axis and a second elongated lobe having a second longitudinal axis, each of said first elongated lobe and said second elongated lobe respectively tapering along said first longitudinal axis and said second longitudinal axis, from a broad end, having a large cross section area to a narrow end, having a small cross section area being smaller than said large cross section area;

said first elongated lobe being spatially fixed relative to said second elongated lobe in a V-shape orientation wherein said first longitudinal axis and said second longitudinal axis intersect at an acute angle, being an apex of said V-shape orientation; and wherein said narrow ends are proximal to said apex.

DETAILED DESCRIPTION

Figure 1:
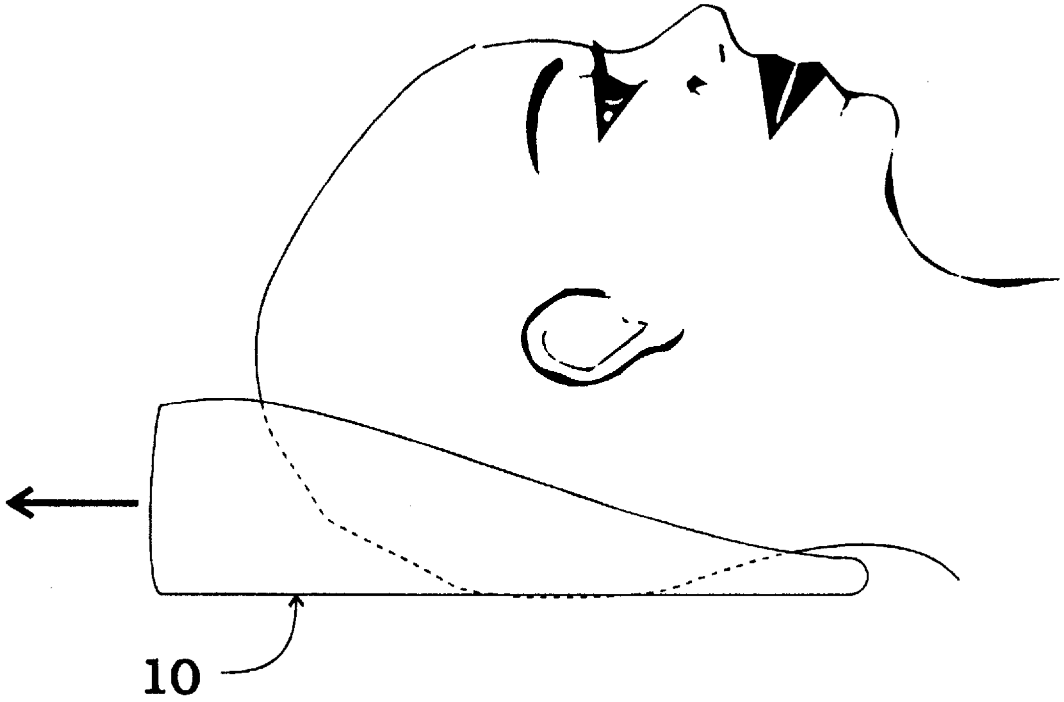
FIG. 1. is a side elevation view of an embodiment of the invention in use on a patient.

As shown in FIGS. 1–4, the headrest 10 generally comprises two elongated, and, for the most part, tapered lobes 12 symmetrically joined at the narrow ends by a neck bar 14. The bottom 16 can be curved, but a flat bottom which allows the headrest to sit evenly on an operating table is preferred. The top and side surfaces of the lobes 18 are generally smooth and curved. In use, the head is placed between the lobes with the back resting on the operating table. The neck bar 14 can have the same shape cross section as the lobes or another shape, such as a circular cross section. The neck bar is sized to fit in the opening created by the natural curvature of the spine between the nape of the neck and the operating table.

Figure 2:
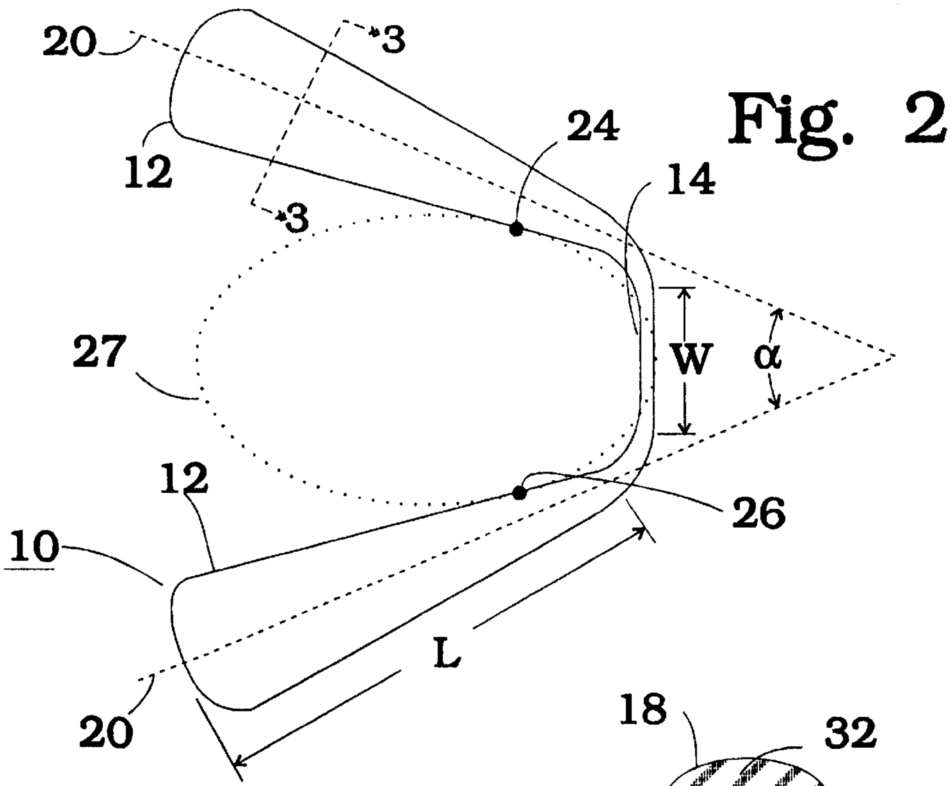
FIG. 2. is a top view of the embodiment shown in FIG. 1.
Figure 4:
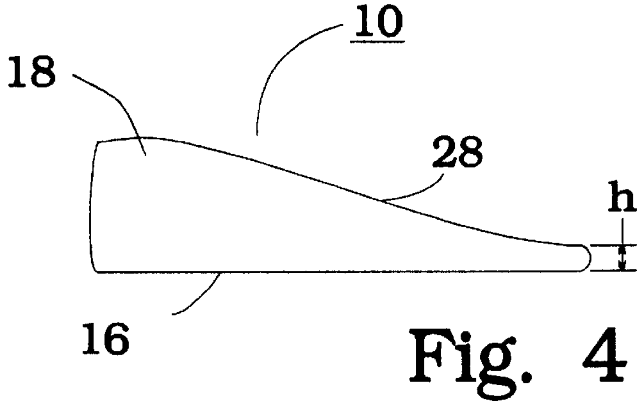
FIG. 4 is a side elevation view of the embodiment shown in FIG. 1.

The lobes have larger cross section area than that of the neck bar. Cross section area refers to the area of a section taken perpendicular to the longitudinal axis of the lobe or neck bar. Generally, the cross section area of the lobes is largest at the broad end far from the neck bar, and the cross section area gradually and progressively diminishes approaching the narrow end. The lobes taper to smoothly transition into the neck bar. The rate at which the lobe tapers can vary nonlinearly with distance from the neck bar to define, for example, a curved lobe height profile 28, as shown in FIG. 4. A straight line lobe height profile, and a profile in which the cross section area is constant for a portion of the lobe length at the broad end and then tapers toward the narrow end, are also acceptable. The lobes are disposed relative to each other in a V-shaped orientation with the narrow ends oriented toward the apex of the V. The shape of the V is characterized by an acute angle, α, between the preferably straight, longitudinal axes of the lobes, 20. If the acute angle, α, is too small, the head will engage the lobes far from the neck bar, which might contact the patient's back between the shoulder blades. If the angle is too large, the head will engage the lobes near the neck bar which reduces stability of head position. Although the neck bar shown in FIG. 2 is straight, it can be curved in the arc of a circle or an ellipse, for example; provided, however, that the curved neck bar does not contact the patient's back between the shoulder blades.

The headrest is used by wedging the patient's head between the lobes. Contact is made at points of tangency, 24 and 26, of each lobe with opposite sides of the head, 27, shown in phantom in FIG. 2. Preferably, the lobes engage the head at or near the mastoid process. This keeps the head from moving from side to side. Due to the progressive taper of the lobes, the head can be gently yet sufficiently tightly wedged so that tilt of the forehead remains fixed in the position desired by the surgeon.

Many combinations of headrest dimensional characteristics, such as the shape of lobe cross section, lobe height profile, angle α, and neck bar shape, will be suitable for use in this invention. One of ordinary skill in the art will be able to select an optimum headrest shape in accordance with the teachings of this disclosure without undue experimentation. Accordingly, it is not intended to limit the present invention to specific combinations of dimensions. However, it has been found that a headrest particularly well adapted to pediatric surgery can be made according to the following parameters. The height, h, of the neck bar, is preferably about 1.2 to about 2 cm. At the end far from the neck bar, the cross section height of the lobes, H, is about 2.5 to about 7.5 cm, and preferably about 3.8 to about 5.1 cm. Acute angle α is at most 90° and preferably is in the range of about 25 to about 65 degrees. Preferably, length of the lobes, L, is about 15 to about 30 cm and width of the neck bar, W, is about 5 to about 10 cm.

The headrest is easily deployed. It may be placed on the operating table prior to arrival of the patient. In that event, the patient's head first is gently placed, between the lobes without contacting the headrest. Then the surgeon orients the head to a desired position, such as an intubating position, and slides the headrest in the direction of the arrow shown in FIG. 1. The lobes thus engage the sides of the head and restrain further movement. If the patient is on the table before the headrest, the surgeon need only slightly elevate the patient's head with one hand in order to slide the neck bar beneath the nape.

After intubation and during the operation, the head position can be adjusted easily. It is a feature of this invention that the top and posterior portions of the head are extensively accessible so that the surgeon can exercise great control while changing the position of the head. Hence, the novel headrest advantageously facilitates the surgeon's ability to complete the operation quickly and safely. The novel headrest is compatible with shoulder rolls which are used to hyperextend the neck and immobilize the head in such operations as tonsillectomies and eye surgery. Some conventional head positioning devices are not suited for use with shoulder rolls.

Figure 3:
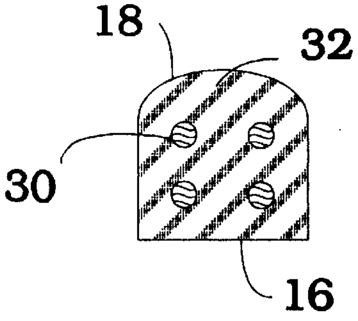
FIG. 3. is a vertical cross section view taken along the line 3—3 in FIG. 2.

The headrest can be molded or sculpted from a single piece of effectively rigid, yet soft, polymeric material, such as a foamed or solid elastomer. It can also be constructed from a rigid frame, such as a single or multiple member wire frame 30 integrally embedded within a layer of soft material 32, as shown in FIG. 3. Alternatively, the wire frame can be wrapped with batting or padding and sealed within a smooth outer layer of tape or upholstery. The headrest is intended for reuse. Accordingly, the outside surface should be of material that resists permeability to fluids normally present during surgery and which is amenable to cleaning between uses. Optionally, the headrest can be fitted with a disposable or launderable cover in the fashion of a pillow case. Also, a simple towel can be laid flat between the headrest and patient to further prevent the headrest from becoming soiled.

Figure 5:
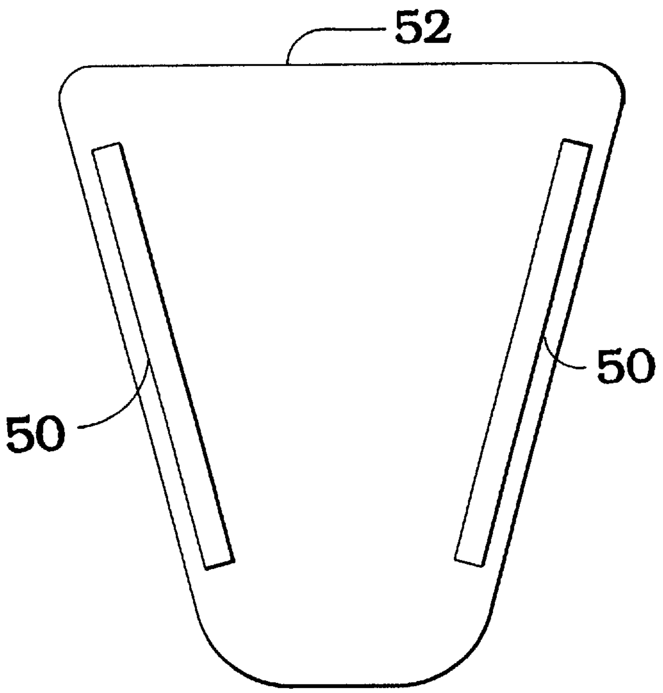
FIG. 5 is a top view of another embodiment of the invention.
Figure 6:
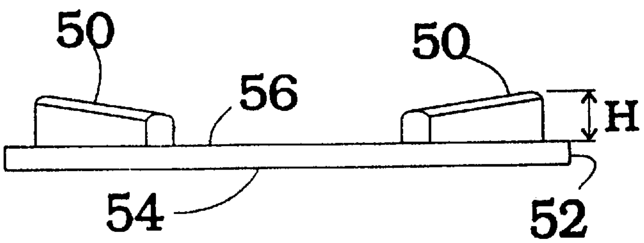
FIG. 6 is a front elevation view of the embodiment shown in FIG. 5.

An alternate embodiment of the invention is shown in FIGS. 5 and 6. Absence of a neck bar provides improved access to the patient's head. The headrest lobes 50 are mounted on a thin pad 52. The thickness of the pad is preferably about 0.6 to about 2 cm. The pad is sufficiently rigid to maintain the lobes in fixed V-shaped relation to each other. The pad has a flat bottom surface 54 which stabilizes the headrest on an operating table. The posterior of the patient's head rests in the central region of flat top surface 56 between lobes 50. The pad is constructed from a soft, resilient material, such as resilient polymer for patient comfort. The height of the lobes H of the embodiment shown in FIG. 6 varies linearly with distance between the lobe ends and therefore, the lobe height profile defines a straight line. A curved lobe height profile can also be used.

I claim:

1. A headrest to hold a head of an unconscious human surgical patient lying supinely on a horizontal table in a selected position, the headrest comprising two elongated lobes, each lobe having a broad end, a narrow end, and a cross section perpendicular to an axis of elongation, the cross section defined by a convexly curved top adapted to form a top surface to contact the head at a point of convex curvature, and a substantially straight bottom adapted to form a flat surface to rest on a flat support, and the axis of elongation being defined by the top surface in a direction from the broad end to the narrow end, each lobe also having a tapered shape defined by a reduction of height of the top surface along the axis of elongation from the broad end to the narrow end; and a connecting means for maintaining the lobes in a fixed spatial relationship wherein the axes of elongation are in horizontal V-shape orientation converging at an acute angle, and wherein each lobe is disposed on an opposite side of the head from the other lobe so that the two lobes are more distant from each other at the broad ends than at the narrow ends, said connecting means being a rigid, slender bar having a long dimension between two bar ends, each lobe being fixedly attached at the narrow end to an opposite bar end, the bar adapted to dispose each lobe on an opposite side of the head from the other lobe so that the narrow ends of the lobes are distant from each other by the long dimension of the bar and the broad ends are distant from each other by a distance greater than the long dimension, the bar also having cross section dimensions small enough to fit the bar within an opening between the patient's neck and the table.

2. The headrest of claim 1 wherein the slender bar has a height of about 1.2 to about 2 cm and a width of about 5 to about 10 cm.

* * * * *